(12) United States Patent
Abraham et al.

(10) Patent No.: US 10,292,948 B2
(45) Date of Patent: May 21, 2019

(54) TAPENTADOL NASAL COMPOSITION

(71) Applicant: Torrent Pharmaceuticals Limited, Ahmedabad (IN)

(72) Inventors: Jaya Abraham, Gandhinagar (IN); Vivek Mishra, Gandhinagar (IN); Vipul Mittal, Gandhinagar (IN); Kiran Chaudhari, Gandhinagar (IN)

(73) Assignee: Torrent Pharmaceuticals Limited, Ahmedabad (IN)

( * ) Notice: Subject to any disclaimer, the term of this patent is extended or adjusted under 35 U.S.C. 154(b) by 0 days.

(21) Appl. No.: 15/866,787

(22) Filed: Jan. 10, 2018

(65) Prior Publication Data

US 2018/0193290 A1   Jul. 12, 2018

Related U.S. Application Data

(60) Provisional application No. 62/444,900, filed on Jan. 11, 2017.

(51) Int. Cl.
| | |
|---|---|
| *A61K 31/137* | (2006.01) |
| *A61K 47/18* | (2017.01) |
| *A61K 47/34* | (2017.01) |
| *A61K 47/38* | (2006.01) |
| *A61K 47/46* | (2006.01) |
| *A61K 9/00* | (2006.01) |
| *A61P 25/04* | (2006.01) |
| *A61K 47/10* | (2017.01) |
| *A61K 9/08* | (2006.01) |

(52) U.S. Cl.
CPC .......... *A61K 31/137* (2013.01); *A61K 9/0043* (2013.01); *A61K 9/08* (2013.01); *A61K 47/10* (2013.01); *A61K 47/18* (2013.01); *A61K 47/34* (2013.01); *A61K 47/38* (2013.01); *A61K 47/46* (2013.01); *A61P 25/04* (2018.01)

(58) Field of Classification Search
CPC ...... A61K 31/137; A61K 47/10; A61K 47/18; A61K 47/34; A61K 47/38; A61K 47/46; A61K 9/0043; A61K 9/08; A61P 25/04
See application file for complete search history.

(56) References Cited

U.S. PATENT DOCUMENTS

| | | | |
|---|---|---|---|
| 5,629,011 | A | 5/1997 | Illum |
| 6,248,737 | B1 | 6/2001 | Buschmann et al. |
| 2006/0110333 | A1 | 5/2006 | Yanagawa |
| 2010/0227921 | A1 | 9/2010 | Franklin et al. |
| 2012/0277319 | A1* | 11/2012 | Steigerwald ......... A61K 9/0053 514/654 |

(Continued)

FOREIGN PATENT DOCUMENTS

WO   WO2005020906 A2   10/2005

OTHER PUBLICATIONS

Somogyi et al., "Pharmacogenetics of Opioids", Clinical Pharmacology & Therapeutics, 2007; 81:3; 429-444.

(Continued)

*Primary Examiner* — Savitha M Rao
(74) *Attorney, Agent, or Firm* — Melissa M. Hayworth; Daniel R. Evans; E. Joseph Gess

(57) ABSTRACT

Disclosed herein are pharmaceutical compositions for nasal administration comprising tapentadol, their preparation and their use in the treatment of pain.

20 Claims, 2 Drawing Sheets

(56) References Cited

U.S. PATENT DOCUMENTS

2014/0170209 A1\* 6/2014 Nadkarni ............ A61K 9/0043
                                                                424/450

OTHER PUBLICATIONS

Dale et al., "Nasal administration of opioids for pain management in adults", Acta Anaesthesiol Scand, 2002; 46; 759-770.
Tapentadol: Clinical Study Report Synopsis R331333-PAI-3003 (KF5503/32), pp. 1-6; Nov. 26, 2007.

\* cited by examiner

TAPENTADOL NASAL COMPOSITION

This application claims the benefit of U.S. Provisional Patent Application No. 62/444,900, filed on Jan. 11, 2017.

FIELD OF THE DISCLOSURE

Disclosed herein are pharmaceutical compositions for nasal administration comprising tapentadol, their preparation and their use in the treatment of pain.

BACKGROUND OF THE DISCLOSURE

Tapentadol is 3-[(1R,2R)-3-(dimethylamino)-1-ethyl-2-methylpropyl]phenol. A particularly preferred form is the hydrochloride salt, 3-[(1R,2R)-3-(dimethylamino)-1-ethyl-2-methylpropyl]phenol monohydrochloride. Tapentadol is highly soluble drug and its solubility is pH dependent. It is considered as BCS class-I drug. Tapentadol hydrochloride may be depicted structurally as follows.

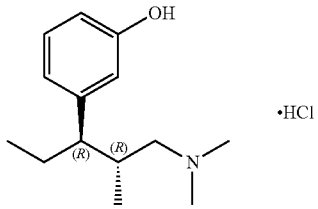

Tapentadol is a centrally acting analgesic having both μ-opioid receptor agonist and noradrenalin (norepinephrine) reuptake inhibition activity with minimal serotonin reuptake inhibition. This dual mode of action makes tapentadol particularly useful in the treatment of both nociceptive pain and neuropathic pain. Clinical trial evidence in acute and chronic non-cancer pain, cancer related pain and neuropathic pain supports an opioid-sparing effect that reduces some of the typical opioid-related adverse effects. Specifically, the reduction in treatment-emergent gastrointestinal adverse effects for tapentadol compared with equi-analgesic pure μ-opioid receptor agonist results in improved tolerability and adherence to therapy.

U.S. Pat. No. 6,248,737 discloses tapentadol and its hydrochloride salt. Tapentadol is available commercially as a brand name NUCYNTA® as 50 mg, 75 mg and 100 mg (free base equivalent) oral tablet, indicated for the relief of moderate to severe acute pain.

Oral administration of tapentadol results in low bioavailability (32%) because of extensive first-pass metabolism where about 97% of the administered tapentadol is metabolized. None of the metabolites contributes to the analgesic activity. Lipid solubility of tapentadol is approximately 2.8, which is comparatively low. Being an opioid analgesic, tapentadol is useful for the treatment of severe pain such as post-operative pain, cancer pain, etc. In such cases nausea and vomiting is a frequently associated problem, and thus, poor patient compliance is seen with oral administration. Moreover, for the treatment of breakthrough pain oral formulations are inadequate because absorption occurs at least 45 minutes after administration, which is not suitable in the treatment of breakthrough pain, as this delay in absorption is typically longer than the episode of breakthrough pain. The maximum serum concentration of tapentadol is typically observed at around 1.25 hours after oral dosing. The bitter taste of tapentadol is not patient friendly, and contributes to poor patient compliance.

Generally, opioids are known to show higher inter-subject variability (Clinical Pharmacology and Therapeutics; 2007; 81; 429-444). It has been observed that the route of administration may have an impact on inter-subject variability. It has been observed that variation of absorption after intranasal route may be a greater than intramuscular or subcutaneous route (Acta Anaesthesiol Scand 2002; 46; 759-770). Like other opioids, tapentadol also has high inter-subject variability, when given orally, as given in Tapentadol clinical study report synopsis R331333-PAI-30003 (KF 5503/32). High clearance of the tapentadol may be one of the reasons of this high inter-subject variability.

Thus, there exists need for an alternative dosage form of tapentadol which overcomes the above problems such as bitter taste, adverse effects, etc., and moreover provides quick onset of action with reduction of inter-subject variability and improved patient compliance.

International Publication No. WO 2005/020906 discloses intranasal opioid composition for pain management with improved bioavailability and improved patient compliance.

U.S. Patent Application Publication No. 2006/0110333 discloses a composition for nasal absorption of opioid comprises calcium carbonate and/or calcium phosphate having particle size of up to 500 μm, with lower risk of developing side effects as compared to oral route.

U.S. Pat. No. 5,629,011 discloses a composition for nasal administration comprises polar metabolite of opioid analgesic consists of glucoronides and ethereal sulphates of opioid analgesics.

U.S. Patent Application Publication No. 2010/0227921 discloses that tapentadol is associated with high inter-patient variability and therefore a uniform patient response may be lacking. Therefore, to overcome the problems, amino acids and peptide carbamate pro-drugs of tapentadol are prepared.

U.S. Patent Application Publication No. 2014/0170209 discloses a nasal composition comprising tapentadol or its pharmaceutically acceptable salts and at least one nasal carrier.

It is well known to the skilled person that apart from many factors, lipid solubility play crucial role in the absorption of drug through nasal mucosa. Drugs with high lipophilicity have higher tendency to get absorbed through nasal mucosa compared to almost negligible absorption of low lipophilicity drugs. It has been tested that, intranasal formulations of low lipophilicity drugs like morphine gives less bioavailability as compared to intravenous administration, when given in solution form. Therefore they are required to be given with agent like chitosan which provides longer time for drug transport across the nasal membrane, before the formulation is cleared by the mucociliary clearance mechanism.

The information disclosed herein is based on the observation that comparable tapentadol pharmacokinetic parameters may be achieved by intranasal administration of a lower tapentadol unit dose in a human when compared to oral administration of a higher tapentadol unit dose of an immediate release dosage form.

SUMMARY OF THE DISCLOSURE

Disclosed herein is, among other things, a unit dose, comprising: tapentadol or a pharmaceutically acceptable salt thereof in an amount that is equivalent to about 19.3 mg tapentadol free base; and at least one nasal carrier; wherein after intranasal administration to the human a tapentadol mean Cmax-value achieved by said unit dose is equivalent to or greater than a tapentadol mean Cmax-value achieved by orally administering to the human an immediate release composition comprising tapentadol or a pharmaceutically acceptable salt thereof in an amount that is equivalent to 50 mg tapentadol free base.

DEFINITIONS

Figure 1:
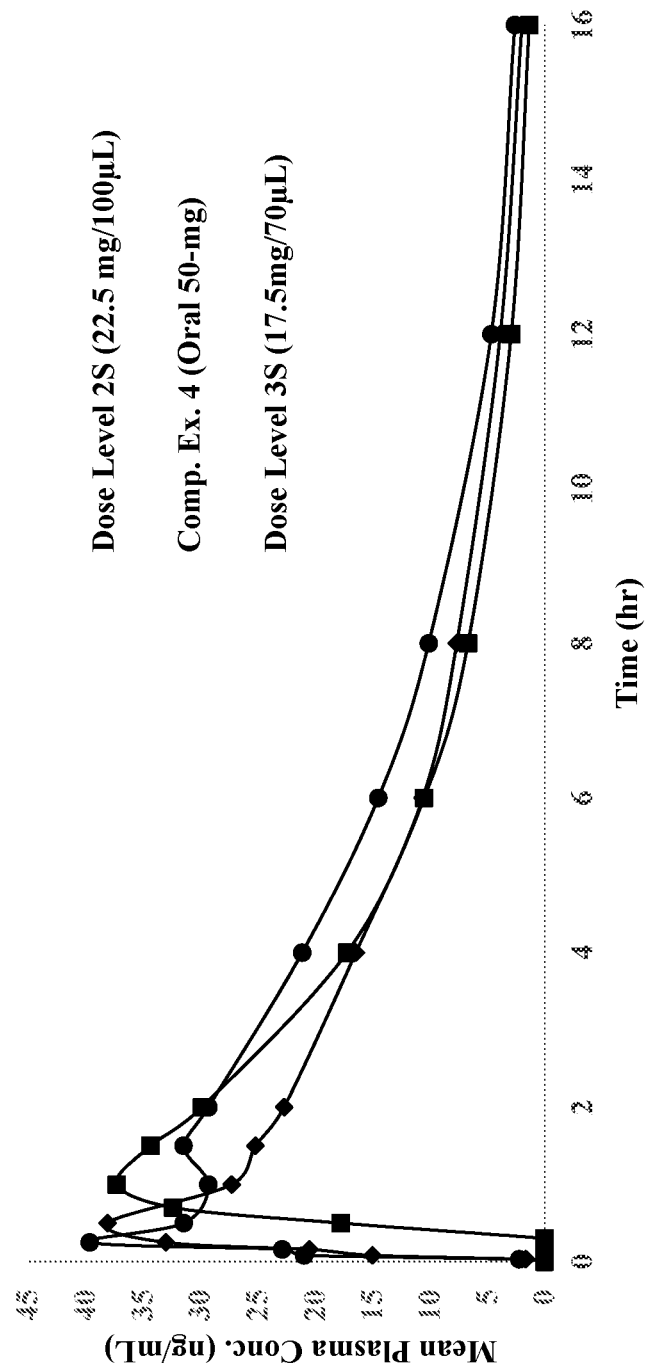
FIG. 1 displays the mean plasma concentration (ng/mL) for Ex. 3 formulation at Dose Level 3S (17.5 mg/70 µL), Ex. 2 formulation at Dose Level 2S (22.5 mg/100 µL), and Comp. Ex. 4 Oral-50 mg (free base equivalent).

The term "about" as used herein refers to variation of 20%. The term "mostly about" as used herein refers to variation of 10%. In some embodiments of present invention, term "about" may preferably be defined as "mostly about".

A stated amount for a compositional ingredient that is not preceded by the term "about" or "mostly about" does not mean that there is no variance for the stated term, as one of ordinary skill would understand that there is always some possibility of a degree of variability generally associated with experimental error.

As disclosed herein, a "unit dose" can be filled in a vial or container which by using suitable nasal spray can be administered to a human. It is possible that a vial may contain volume of composition that has multiple "unit doses" and delivers unit dose in single or multiple sprays.

The term "administration" or "administered" or "administering" as used herein refers to administration of a unit dose of a composition described herein to a human. A skilled person will understand that said unit dose can be administered in a single spray to one nostril. A skilled person will also understand that said unit dose can be administered in a single spray to each nostril, which is synonymous with administration to both nostrils. The unit dose may be administration over repeated time intervals, as needed.

The expression "immediate release composition comprising tapentadol" as used herein refers to Nucynta® for oral administration.

The concentration unit "% w/v" is a measure of the weight amount of a specified ingredient based on the total volume of the composition.

The pharmaceutically acceptable salts of tapentadol, as described herein, are acid addition salts wherein acid is selected from hydrochloric acid, hydrobromic acid, embonic acid, (2S,3S)-dibenzoyltartaric acid, dibenzoyltartaric acid, sebacic acid, 1-hydroxy-naphthoic acid, phosphoric acid, L-(+)-tartaric acid, lysinic acid, L-lysinic acid, D-(+)-malic acid, 4-methylbenzenesulfonic acid, ethanesulfonic acid, benzoic acid, cinnamic acid, L-(+)-lactic acid, S-(+)-mandelic acid, (+)-camphor-10-sulfonic acid, gluconic acid, L-(+)-ascorbic acid, ascorbic acid, palmitic acid, naphthalene-1,5-disulfonic acid, hexanoic acid, oleic acid, stearic acid, gentisic acid, octanoic acid, decanoic acid, nitric acid, orotic acid, mucic acid, alginic acid and acesulfamic acid, nicotinic acid, hydrogen bromide, sulfuric acid, acetic acid, propionic acid, oxalic acid, succinic acid, fumaric acid, maleic acid, hippuric acid, lactic acid, mandelic acid, malonic acid, malic acid, tartaric acid, methanesulfonic acid, citric acid, lactic acid. Preferably hydrochloric acid addition salt of tapentadol is used for compositions described herein.

The term "composition" as used herein is defined as a solution, suspension, or dispersion.

The term "Crystal growth inhibitor" as used herein is defined as an agent, which facilitates formation of a homogenous nasal composition of tapentadol and prevents crystal formation.

The use of the terms "a" and "an" and "the" and similar references in the context of the terms recited herein are to be construed to cover both the singular and the plural, unless otherwise indicated herein or clearly contradicted by context.

DETAILED DESCRIPTION OF THE DISCLOSURE

The following paragraphs detail various embodiments of the disclosure. For the avoidance of doubt, it is specifically intended that any particular feature(s) described individually in any one of these paragraphs (or part thereof) may be combined with one or more other features described in one or more of the remaining paragraphs (or part thereof). In other words, it is explicitly intended that the features described below individually in each paragraph (or part thereof) represent aspects of the disclosure that may be taken in isolation and/or combined with other aspects of the disclosure. The skilled person will appreciate that the claimed subject matter extends to such combinations of features and that these have not been recited in detail here in the interests of brevity.

Embodiment A

A1. A unit dose, comprising: tapentadol or a pharmaceutically acceptable salt thereof in an amount that is equivalent to about 19.3 mg tapentadol free base; and at least one nasal carrier; wherein after intranasal administration to the human a tapentadol mean Cmax-value achieved by said unit dose is equivalent to or greater than a tapentadol mean Cmax-value achieved by orally administering to the human an immediate release composition comprising tapentadol or a pharmaceutically acceptable salt thereof in an amount that is equivalent to 50 mg tapentadol free base.

A2. The unit dose according to A1, wherein intranasal administration of the unit dose to the human provides tapentadol mean Cmax-value that ranges from about 40 ng/mL to about 65 ng/mL.

A3. The unit dose according to A1, wherein a ratio of the tapentadol mean Cmax-value achieved by said intranasal administration of the unit dose to the tapentadol mean Cmax-value achieved by said oral administration ranges from about 1.0 to about 2.0.

A4. The unit dose according to A1, wherein intranasal administration of the unit dose to the human provides tapentadol mean $AUC_{0-6}$-value that ranges from about 115 hr*ng/mL to about 182 hr*ng/mL.

A5. The unit dose according to A1, wherein a ratio of the tapentadol mean $AUC_{0-6}$-value achieved by said intranasal administration of the unit dose to the tapentadol mean $AUC_{0-6}$-value achieved by said oral administration ranges from about 0.9 to about 1.7.

A6. The unit dose according to A1, wherein intranasal administration of the unit dose to the human provides the mean Tmax-value about 1 hr or less.

A7. The unit dose according to A1, wherein intranasal administration of the unit dose to the human provides the mean Tmax-value about 0.2 hr to about 0.8 hr.

A8. The unit dose according to A1, wherein the immediate release composition comprises tapentadol hydrochloride.

Embodiment B

B1. A unit dose, comprising: tapentadol or a pharmaceutically acceptable salt thereof in an amount that is equivalent to about 19.3 mg tapentadol free base; and at least one nasal carrier; wherein after intranasal administration to each nostril of the human a tapentadol mean Cmax-value achieved by said unit dose is equivalent to or greater than a tapentadol mean Cmax-value achieved by orally administering to a human an immediate release composition comprising tapentadol or a pharmaceutically acceptable salt thereof in an amount that is equivalent to about 100 mg tapentadol free base.

B2. The unit dose according to B1, wherein intranasal administration of the unit dose to each nostril of the human provides a tapentadol mean Cmax-value that ranges from about 98 ng/mL to about 155 ng/mL.

B3. The unit dose according to B1, wherein a ratio of the tapentadol mean Cmax-value achieved by said intranasal administration of the unit dose to each nostril to the tapentadol mean Cmax-value achieved by said oral administration ranges from about 1 to about 2.

B4. The unit dose according to B1, wherein intranasal administration of the unit dose to each nostril of the human provides tapentadol mean $AUC_{0-6}$-value that ranges from about 230 hr*ng/mL to about 365 hr*ng/mL.

B5. The unit dose according to B1, wherein a ratio of the tapentadol mean $AUC_{0-6}$-value achieved by said intranasal administration of the unit dose to each nostril of the human to the tapentadol mean $AUC_{0-6}$-value achieved by said oral administration ranges from about 0.9 to about 2.0.

B6. The unit dose according to B1, wherein intranasal administration of the unit dose to each nostril of the human provides the Tmax-value about 1 hr or less.

B7. The unit dose according to B1, wherein intranasal administration of the unit dose to the human provides the mean Tmax-value about 0.2 hr to about 0.6 hr.

B8. The unit dose according to B1, wherein the immediate release composition comprises tapentadol hydrochloride.

Embodiment C

C1. A unit dose, comprising: tapentadol or a pharmaceutically acceptable salt thereof in an amount that is equivalent to about 19.3 mg tapentadol free base; and at least one nasal carrier, wherein the therapeutic efficacy of tapentadol achieved by intranasally administering to one nostril or both nostrils said unit dose in a human for the treatment of pain is equivalent to the therapeutic efficacy achieved by orally administering to a human an immediate release composition comprising tapentadol or a pharmaceutically acceptable salt thereof in an amount that is equivalent to about 50 mg and about 100 mg tapentadol free base, respectively.

C2. A method of treating pain in a human in need thereof, which comprises: intranasally administering to the human the unit dose of C1.

C3. A method of treating pain in a human in need thereof, which comprises: intranasally administering to each nostril of the human the unit dose of C1.

C4. The unit dose according to C1, wherein the immediate release composition comprises tapentadol hydrochloride.

Embodiment D

D1. A method of treating pain in a human in need thereof, which comprises: intranasally administering to the human a dose comprising tapentadol or a pharmaceutically acceptable salt thereof; wherein the amount of tapentadol in said dose is equivalent to about 19.3 mg tapentadol free base; and wherein after intranasal administration of the dose, a tapentadol mean Cmax-value achieved by said intranasal administration is equivalent to or greater than a tapentadol mean Cmax-value achieved by orally administering to a human an immediate release composition comprising tapentadol or a pharmaceutically acceptable salt thereof in an amount that is equivalent to 50 mg tapentadol free base.

D2. The method of D1 comprising intranasally administering the dose to the human, wherein the tapentadol mean Cmax-value achieved by said intranasal administration ranges from about 40 ng/mL to about 65 ng/mL.

D3. The method of D1 comprising intranasally administering the dose to the human, wherein a ratio of the tapentadol mean Cmax-value achieved by said intranasal administration to the tapentadol Cmax-value achieved by said oral administration ranges from about 1.0 to about 2.0.

D4. The method of D1 comprising intranasally administering the dose to each nostril of the human, wherein the tapentadol mean Cmax-value achieved by said intranasal administration ranges from about 98 ng/mL to about 155 ng/mL.

D5. The method of D4 comprising intranasally administering the dose to each nostril of the human, wherein a ratio of the tapentadol mean Cmax-value achieved by said intranasal administration to the tapentadol mean Cmax-value achieved by said oral administration ranges from about 2.5 to about 5.0.

D6. The method of D1 comprising intranasally administering the dose to the human, wherein the Tmax-value achieved by said intranasal administration is less than about 1 hr.

D7. The method of D1 comprising intranasally administering the dose to the human, wherein the Tmax-value achieved by said intranasal administration ranges from about 0.2 hr to about 0.8 hr.

D8. The method of D1 comprising intranasally administering the dose to the human, wherein the tapentadol mean $AUC_{0-6}$-value achieved by said intranasal administration ranges from about 115 hr*ng/mL to about 182 hr*ng/mL.

D9. The method of D1 comprising intranasally administering the dose to the human, wherein a ratio of the tapentadol mean $AUC_{0-6}$-value achieved by said intranasal administration to the tapentadol mean $AUC_{0-6}$-value achieved by said oral administration ranges from about 0.9 to about 1.7.

D10. The method of D1 comprising intranasally administering the dose to each nostril of the human, wherein the tapentadol mean $AUC_{0-6}$-value achieved by said intranasal administration ranges from about 230 hr*ng/mL to about 365 hr*ng/mL.

D11. The method of D1 comprising intranasally administering the dose to each nostril of the human, wherein a ratio of the tapentadol mean $AUC_{0-6}$-value achieved by said intranasal administration to the tapentadol mean $AUC_{0-6}$-value achieved by said oral administration ranges from about 1.5 to about 3.5.

D12. The method according to D1, wherein the immediate release composition comprises tapentadol hydrochloride.

Embodiment E

E1. A method of treating pain in a human in need thereof, which comprises: intranasally administering to each nostril of the human a dose comprising tapentadol or a pharmaceutically acceptable salt thereof; wherein the amount of tapentadol in the dose is equivalent to about 19.3 mg tapentadol free base; and wherein after administration of the dose to each nostril a tapentadol Cmax-value achieved by said intranasal administration is equivalent to or greater than a tapentadol Cmax-value achieved by orally administering to a human an immediate release composition comprising tapentadol or a pharmaceutically acceptable salt thereof in an amount that is equivalent to 100 mg tapentadol free base.

E2. The method of E1, wherein the tapentadol mean Cmax-value achieved by said intranasal administration ranges from about 98 ng/mL to about 155 ng/mL.

E3. The method of E1, wherein a ratio of the tapentadol mean Cmax-value achieved by said intranasal administration to the tapentadol mean Cmax-value achieved by said oral administration ranges from about 1.0 to about 2.0.

E4. The method of E1, wherein the Tmax-value achieved by said intranasal administration is less than about 1 hr.

E5. The method of E1, wherein the Tmax-value achieved by said intranasal administration ranges from about 0.2 hr to about 0.6 hr.

E6. The method of E1, wherein the tapentadol mean $AUC_{0-6}$-value achieved by said intranasal administration ranges from about 230 hr*ng/mL to about 365 hr*ng/mL.

E7. The method of E1, wherein a ratio of the tapentadol mean $AUC_{0-6}$-value achieved by said intranasal administration to the tapentadol mean $AUC_{0-6}$-value achieved by said oral administration ranges from about 0.9 to about 2.0.

E8. The method according to E1, wherein the immediate release composition comprises tapentadol hydrochloride.

Embodiment F

F1. An intranasal composition for treating pain in a human which provides a dose reduction of tapentadol compared to an immediate release oral composition comprising a therapeutically effective dose of tapentadol or a pharmaceutically acceptable salt thereof, the intranasal composition comprising: a therapeutically effective dose of tapentadol or a pharmaceutically acceptable salt thereof and a pharmaceutically acceptable nasal carrier; wherein the ratio of the amount of tapentadol, based on the amount of tapentadol free base, in the intranasal dose to the amount of tapentadol, based on the amount of tapentadol free base, in the oral dose is selected from the group consisting of about 1:1.5 or less, about 1:2 or less, about 1:2.5 or less, about 1:3 or less, and about 1:3.5 or less; and wherein the intranasal dose and the oral dose, when administered to the human, exhibit substantially equivalent bioavailability.

F2. The composition according to F1, wherein the intranasal composition is for treating pain in the human by producing substantially equivalent bioavailability of tapentadol in the human as the oral composition.

F3. The composition according to F1, wherein the amount of tapentadol, based on the amount of tapentadol free base, in the oral dose is from about 50 to about 150 mg, or from about 50 to about 100 mg, or from about 50 to about 75 mg.

F4. The composition according to F1, wherein each of the intranasal composition and the oral composition comprises tapentadol hydrochloride, and wherein the amount of tapentadol hydrochloride in the oral dose is about 58 to 117 mg and the amount of tapentadol hydrochloride in the intranasal dose is selected from the group consisting of about 15 to about 20 mg, about 20 to about 22.5 mg, about 22.5 to about 25 mg, about 25 mg to about 30 mg, about 30 mg to about 35 mg, about 35 mg to 40 mg, about 40 mg to 45 mg and about 45 mg to 50 mg, and wherein the oral composition is an immediate release composition.

F5. The composition according to F1, wherein the intranasal composition comprises tapentadol hydrochloride and a nasal carrier.

F6. The composition according to F1, wherein the bioavailability of the intranasal dose and the oral dose are measured after single dose administration to human.

F7. The composition according to F1, wherein the intranasal composition is for providing relief of moderate to severe pain, preferably acute pain.

F8. The composition according to F1, wherein the immediate release oral composition comprises tapentadol hydrochloride.

Embodiment G

G1. An intranasal composition for treating pain in a human that provides substantially equivalent therapeutic efficacy to the therapeutic efficacy provided by an immediate release oral composition comprising a therapeutically effective dose of tapentadol or a pharmaceutically acceptable salt thereof, the intranasal composition comprising: a therapeutically effective dose of tapentadol or a pharmaceutically acceptable salt thereof and a pharmaceutically acceptable nasal carrier; wherein the ratio of the amount of tapentadol, based on the amount of tapentadol free base, in the intranasal dose to the amount of tapentadol, based on the amount of tapentadol free base, in the oral dose is selected from the group consisting of about 1:1.5 or less, about 1:2 or less, about 1:2.5 or less, about 1:3 or less, and about 1:3.5 or less; and wherein the intranasal dose and the oral dose, when administered to the human, exhibit substantially equivalent bioavailability.

G2. The composition according to G1, wherein the amount of tapentadol, based on the amount of tapentadol free base, in the oral dose is from about 50 to about 150 mg, or from about 50 to about 100 mg, or from about 50 to about 75 mg.

G3. The composition according to G1, wherein each of the intranasal composition and the oral composition comprises tapentadol hydrochloride, and wherein the amount of tapentadol hydrochloride in the oral dose is about 58 to about 117 mg and the amount of tapentadol hydrochloride in the intranasal dose is selected from the group consisting of about 15 to about 20 mg, about 20 to about 22.5 mg, about 22.5 to about 25 mg, about 25 mg to about 30 mg, about 30 mg to about 35 mg, about 35 mg to 40 mg, about 40 mg to about 45 mg and about 45 mg to about 50 mg, and wherein the oral composition is an immediate release composition.

G4. The composition according to G1, wherein the intranasal composition comprises tapentadol hydrochloride and a nasal carrier.

G5. The composition according to G1, wherein the bioavailability of the intranasal dose and the oral dose are measured after single dose administration to human.

G6. The composition according to G1, wherein the intranasal composition is for providing relief of moderate to severe pain, preferably acute pain.

G7. The composition according to G1, wherein the immediate release oral composition comprises tapentadol hydrochloride.

Embodiment H

H1. A kit for administration of tapentadol or a pharmaceutically acceptable salt thereof to a human to treat pain while providing a dose reduction of tapentadol compared to an immediate release oral composition comprising a therapeutically effective dose of tapentadol or a pharmaceutically acceptable salt thereof, said kit comprising: (i) a composition for intranasal administration comprising therapeutically effective dose of tapentadol or a pharmaceutically acceptable salt thereof and a pharmaceutically acceptable nasal carrier; and (ii) a container equipped with a spray pump adapted to deliver the composition into one nostril or each nostril of the human, wherein the container is configured such that it delivers the therapeutically effective dose in one spray or in two sprays, and wherein the ratio of the amount of tapentadol, based on the amount of tapentadol free base, in the intranasal dose to the amount of tapentadol, based on the amount of tapentadol free base, in the oral dose is selected from the group consisting of about 1:1.5 or less, about 1:2 or less, about 1:2.5 or less, about 1:3 or less, and about 1:3.5 or less, and wherein the intranasal dose and the oral dose, when administered to the human, exhibit substantially equivalent bioavailability.

H2. The kit according to H1, wherein the spray pump is a metered multi-dose spray pump that is adapted to deliver the therapeutically effective intranasal dose in one spray.

H3. The kit according to H1, wherein the amount of tapentadol, based on the amount of tapentadol free base, in the oral dose is from about 50 to about 150 mg, or from about 50 to about 100 mg, or from about 50 to about 75 mg.

H4. The kit according to H1, wherein each of the intranasal composition and the oral composition comprises tapentadol hydrochloride, wherein the amount of tapentadol hydrochloride in the oral dose is about 58 to about 117 mg and the amount of tapentadol hydrochloride in the intranasal dose is selected from the group consisting of about 15 to about 20 mg, about 20 to about 22.5 mg, about 22.5 to about 25 mg, about 25 mg to about 30 mg, about 30 mg to about 35 mg, about 35 mg to about 40 mg, about 40 mg to about 45 mg and about 45 mg to about 50 mg, and wherein the oral composition is an immediate release composition.

H5. The kit according to H1, wherein the intranasal dose provides relief of moderate to severe pain, preferably acute pain.

H6. The kit according to H1, wherein the composition comprises an aqueous solution of tapentadol or tapentadol hydrochloride.

H7. The kit according to H1, wherein the bioavailability of the intranasal dose and the oral dose are measured after single dose administration to human.

H8. The kit according to H1, wherein the immediate release oral composition comprises tapentadol hydrochloride.

Embodiment I

I1. A method for treating pain in a human in need thereof, which provides a dose reduction of tapentadol compared to the administration of an immediate release oral composition comprising a therapeutically effective dose of tapentadol or a pharmaceutically acceptable salt thereof, the method comprising: intranasally administering to said human a composition comprising a therapeutically effective dose of tapentadol or a pharmaceutically acceptable salt thereof and a pharmaceutically acceptable nasal carrier; wherein the ratio of the amount of tapentadol, based on the amount of tapentadol free base, in the intranasal dose to the amount of tapentadol, based on the amount of tapentadol free base, in the oral dose is selected from the group consisting of about 1:1.5 or less, about 1:2 or less, about 1:2.5 or less, about 1:3 or less, and about 1:3.5 or less; and wherein the intranasal dose and the oral dose, when administered to the human, exhibit substantially equivalent bioavailability.

I2. The method according to I1, wherein the method is for treating pain by producing substantially equivalent bioavailability of tapentadol in human as the oral composition.

I3. The method according to I1, wherein the amount of tapentadol, based on the amount of tapentadol free base, in the oral dose is from about 50 to about 150 mg, or from about 50 to about 100 mg, or from about 50 to about 75 mg.

I4. The method according to I1, wherein each of the intranasal composition and the oral composition comprises tapentadol hydrochloride, and wherein the amount of tapentadol in the oral dose is about 58 to about 117 mg and the amount of tapentadol in the intranasal dose is selected from the group consisting of about 15 to about 20 mg, about 20 to about 22.5 mg, about 22.5 to about 25 mg, about 25 mg to about 30 mg, about 30 mg to about 35 mg, about 35 mg to about 40 mg, about 40 mg to about 45 mg and about 45 mg to about 50 mg, and wherein the oral composition is an immediate release composition.

I5. The method according to I1, wherein the intranasal composition comprises tapentadol hydrochloride and a nasal carrier.

I6. The method according to I1, wherein the bioavailability of the intranasal dose and the oral dose are measured after single dose administration to human.

I7. The method according to I1, wherein the method provides relief of moderate to severe pain, preferably acute pain.

I8. The method according to I1, wherein the immediate release oral composition comprises tapentadol hydrochloride.

Embodiment J

J1. A method for treating pain in a human which provides therapeutic efficacy substantially equivalent to the therapeutic efficacy provided by the administration of an immediate release oral composition comprising a therapeutically effective dose of tapentadol or a pharmaceutically acceptable salt thereof, the method comprising: intranasally administering to said human a composition comprising a therapeutically effective dose of tapentadol or a pharmaceutically acceptable salt thereof and a pharmaceutically acceptable nasal carrier; wherein the ratio of the amount of tapentadol, based on the amount of tapentadol free base, in the intranasal dose to the amount of tapentadol, based on the amount of tapentadol free base, in the oral dose is selected from the group consisting of about 1:1.5 or less, about 1:2 or less, about 1:2.5 or less, about 1:3 or less, and about 1:3.5 or less; and wherein the intranasal dose and the oral dose.

J2. The method according to J2, wherein the amount of tapentadol, based on the amount of tapentadol free base, in the oral dose is from about 50 to about 150 mg, or from about 50 to about 100 mg, or from about 50 to about 75 mg.

J3. The method according to J1, wherein each of the intranasal composition and the oral composition comprises tapentadol hydrochloride, and wherein the amount of tapentadol hydrochloride in the oral dose is about 58 to about 117 mg and the amount of tapentadol hydrochloride in the intranasal dose is selected from the group consisting of about 15 to about 20 mg, about 20 to about 22.5 mg, about 22.5 to about 25 mg, about 25 mg to about 30 mg, about 30 mg to about 35 mg, about 35 mg to 40 mg, about 40 mg to 45 mg and about 45 mg to about 50 mg, and wherein the oral composition is an immediate release composition.

J4. The method according to J1, wherein the intranasal composition comprises tapentadol hydrochloride and a nasal carrier.

J5. The method according to J1, wherein the bioavailability of the intranasal dose and the oral dose are measured after single dose administration to human.

J6. The method according to J1, wherein the method provides relief of moderate to severe pain, preferably acute pain.

J7. The method according to J1, wherein the immediate release oral composition comprises tapentadol hydrochloride.

Embodiment K

K1. A method of increasing the bioavailability of tapentadol in a human, comprising intranasally administering to said human a pharmaceutical composition comprising a therapeutically effective dose of tapentadol or a pharmaceutically acceptable salt thereof and a pharmaceutically acceptable nasal carrier, wherein the bioavailability of the intranasal dose is increased compared to the bioavailability of an equivalent dose of an immediate release oral composition comprising a therapeutically effective dose of tapentadol or a pharmaceutically acceptable salt thereof.

K2. The method according to K1, wherein the ratio of the mean $AUC_{0-6}$ of tapentadol after the intranasal administration to the mean $AUC_{0-6}$ of tapentadol after the oral administration is selected from the group consisting of at least about 1.5:1, at least about 2:1, at least about 2.5:1, at least about 3:1 and at least about 3.5:1.

K3. The method according to K1, wherein the intranasal composition comprises tapentadol hydrochloride and a nasal carrier.

K4. The method according to K1, wherein the mean $AUC_{0-6}$ of the intranasal dose and the mean $AUC_{0-6}$ of the oral dose are measured after single dose administration to human.

K5. The method according to K1, wherein immediate release oral composition comprises tapentadol hydrochloride.

In a general embodiment, unit dose, dose or therapeutically effective dose according to any of the embodiments described herein above may comprise tapentadol hydrochloride in an amount that is equivalent to about 15 mg to about 20 mg of tapentadol free base or any value in between, including, for example 15.0, 15.5, 16.0, 16.5, 17.0, 17.5, 18.0, 18.5 . . . up to 20.0 mg.

Compositions

Compositions disclosed herein contain tapentadol or its pharmaceutically acceptable salt(s) in an amount equivalent to about 0.9 to about 49.9% w/v of tapentadol free base, or any values in between, including, for example, 1.0, 1.1, 1.2, . . . up to 15, 15.1, 15.2, . . . up to 19.3, 19.4, 19.5, . . . up to 21.5, 21.6, 21.7, . . . up to 33.1, 33.2, 33.3, . . . up to 49.9% w/v. Compositions exemplified herein contain an amount of tapentadol free base of 15% w/v, 19.3% w/v, 21.5% w/v, and 33.1% w/v. Most preferably, composition contains about 19.3% w/v of tapentadol free base.

Compositions or unit dose according to any of the embodiment are comprised of a nasal carrier (or pharmaceutically acceptable nasal carrier) selected from a mucoadhesive agent, a solubilizer, a sweetener, a preservative, a flavoring agent, and a vehicle.

Examples of mucoadhesive agent include, but are not limited to such as polyacrylic polymers like carbopols, polycarbophil, carboxymethylcellulose or its pharmaceutically acceptable salt, microcrystalline cellulose, hydroxyethylcellulose, hydroxypropyl cellulose, hydroxypropylmethyl cellulose (i.e., hypromellose), methylcellulose, poloxamers, pectin, xanthan gums, alginates, gelatin alone or in any combination thereof. A preferred mucoadhesive agent is selected from hydroxypropylmethyl cellulose and carboxymethyl cellulose or its pharmaceutically acceptable salt.

Nasal compositions disclosed herein contain about 0.05 to about 5% w/v of a mucoadhesive agent or any values between, including, for example, 0.1, 0.15, 0.2, 0.25, 0.30, 0.35, 0.4, . . . up to 5% w/v. An amount of a mucoadhesive agent exemplified herein is about 0.1% w/v of hydroxypropyl methyl cellulose.

Examples of solubilizers (or crystal growth inhibitors) include, but are not limited to d-alpha tocopheryl polyethylene glycol 1000 succinate (Vitamin E TPGS), macrogol (15)-hydroxystearate (Solutol HS 15), polyoxyethylene-polyoxypropylene copolymer (Poloxamer, Pluronic, such as poloxamer 188), PEO-PLLA diblock copolymer, PEG-PLGA-PEG triblock, copolymer, cyclodextrins, hydroxypropyl betadex, polyoxyethylene castor oil derivatives, povidone, sulfobutylether-b-cyclodextrin, tricaprylin, triolein, glyceryl monostearate, sorbitan esters (sorbitan fatty acid esters), polyoxyethylene fatty acid esters, polysorbate 80, polysorbate 20 or macrogol-15-hydroxysterate, alone or in combination thereof. A preferred solubilizer is polyoxyethylene-polyoxypropylene copolymer, such as, poloxamer 188.

It is observed that increase in concentration of the tapentadol in the solution leads to formation of crystals, when stored for extended duration (for more than 3 days). This makes the formulation non-homogeneous and therefore non-suitable for nasal administration. This crystal growth may further lead to altered therapeutic effect of the drug. The solubilizer may function as a crystal growth inhibitor, which permits manufacture of a composition having a higher concentration and that permits long term storage.

Nasal compositions disclosed herein contain from about 0.2 to about 10.0% w/v of a solubilizer or any values between, including, for example, 0.3, 0.4, 0.5, 0.6, 0.7, 0.8, 0.9, . . . up to 10.0% w/v. An amount of a solubilizer exemplified herein is about 0.6% w/v.

The sweetener is selected from the group comprising of aspartame, saccharin sodium, acesulfame potassium, dried invert sugar, dextrose, glucose, fructose, galactose, levulose, maltose, neotame, sucralose, neotame and mixture thereof. Preferred sweetener is sucralose. Another preferred sweetener is neotame.

Nasal compositions disclosed herein contain from about 0.1% to about 1% of a sweetener or any values between, including, for example, 0.2, 0.3, 0.4, 0.5, 0.6, . . . up to 1.0% w/v. An amount of a sweetener exemplified herein is about 0.5% w/v.

Suitable preservatives include, but are not limited to, benzalkonium chloride, sodium benzoate, methyl, ethyl, propyl or butyl paraben, benzyl alcohol, phenylethyl alcohol, benzethonium chloride, chlorobutanol, potassium sorbate or combination thereof. A preferred preservative is benzalkonium chloride.

Nasal compositions disclosed herein contain from about 0.01 to about 1% w/v of a preservative or any values between, including, for example, 0.02, 0.03, 0.04, 0.05, . . . up to 0.1, and 0.2, 0.3, 0.4, 0.5, 0.6, up to 1% w/v. An amount of a sweetener exemplified herein is about 0.5% w/v.

Examples of flavoring agent(s) include, but are not limited to flavor anise, flavor apple, flavor apricot, flavor Banana, flavor bitter mask, flavor buttermint, flavor citrus, flavor orange, flavor menthol mint, flavor mint, flavor peppermint, flavor spearmint, alone or in any combination thereof. A preferred flavor is flavor spearmint.

Nasal compositions disclosed herein contain from about 0.01% w/v to about 0.5% w/v of a flavoring agent or any values between, including, for example, 0.02, 0.03, 0.04, 0.05, 0.6, 0.07, 0.08, 0.09, 0.10, . . . up to 0.5% w/v. An amount of a flavoring agent exemplified herein is about 0.1% w/v.

Examples of vehicles include, but are not limited to, saline, water, dextrose or combinations thereof. A preferred vehicle is purified water. The amount of vehicle depends on the amounts of the other ingredients found in the nasal composition. The amount of vehicle is a sufficient amount (q.s.) that is required to establish a specified volume.

The pH of compositions described herein may be about 3.0 to about 7.4 and all values in between, including, for example, 4.1, 4.2, 4.3, 4.4, 4.5, 4.6, 4.7, . . . up to 7.4. A preferred pH of compositions described herein may be about 4.5. The pH may be adjusted using a pH adjusting agent, including, for example, hydrochloric acid or sodium hydroxide. In certain instance, it may be useful to include a buffering agent in an amount that preferably does not irritate the nasal mucosa. A buffering agent includes an agent that resists changes to pH. Exemplary buffering agents include, but are not limited to, salts of citrate, acetate, or phosphate. More preferred buffering agents are selected from sodium citrate, sodium acetate, sodium phosphate, and/or combinations thereof.

Thus, the unit dose or composition according to any of the embodiment(s) disclosed herein comprising tapentadol or a pharmaceutically acceptable salt thereof in an amount equivalent to about 19.3% w/v tapentadol free base and a nasal carrier, wherein the nasal carrier is selected from about 0.05 to about 5% w/v of a mucoadhesive agent; from about 0.2 to about 10.0% w/v of a solubilizer; from about 0.1% to about 1% of a sweetener; from about 0.01 to about 1% w/v of a preservative, from about 0.01% w/v to about 0.5% w/v of a flavoring agent, and a sufficient amount of a water vehicle. Preferably, unit dose or composition comprises mucoadhesive agent selected from hydroxypropylmethyl cellulose and carboxymethyl cellulose or its pharmaceutically acceptable salt, the solubilizer comprises a poloxamer, the sweetener selected from sucralose and neotame, preservative comprises benzalkonium chloride and the flavoring agent comprises a spearmint flavor.

Most preferably, unit dose or composition according to any of the embodiments comprises nasal carrier selected from about 0.1% w/v hydroxypropylmethyl cellulose, about 0.6% w/v of a poloxamer, about 0.5% w/v of a sweetener, about 0.02% w/v of a preservative, and a sufficient amount of a water vehicle.

Compositions described herein provide a quick onset of action as compared to an immediate release oral composition, in which the Cmax can be achieved in a shorter period of time as compared to oral administration. Composition or unit dose disclosed herein provides mean Cmax-value that ranges from about 40 ng/mL to about 65 ng/mL or about 98 ng/mL to about 155 ng/mL; mean $AUC_{0-6}$-value that ranges from about 115 hr*ng/mL to about 182 hr*ng/mL or about 230 hr*ng/mL to about 365 hr*ng/mL and Tmax-value about 1 hr or less.

Compositions disclosed herein provide for a unit dose in a volume of from about 25 µL to about 150 µL, or any values between, including, for example, 30 µL, 35 µL, 40 µL, . . . up to 70 µL, 75 µL, 80 µL, . . . up to 100 µL, 105 µL, 110 µL, . . . up to 150 µL. Exemplified embodiments described herein administer a unit dose of either about 70 µL or about 100 µL or about 140 µL, to one or both nostrils. The compositions or unit dose described herein, when administered intranasally has a spray having an ovality ratio between about 1 to about 2, or between about 1 to about 1.5 or between about 1 to about 1.3 when measured at about 2.5 cm, and wherein the spray produces droplets of which less than about 10%, preferably less than about 5%, more preferably less than about 2%, have a diameter of less than about 10 µm.

The compositions or unit dose described herein, when administered intranasally has a spray comprising a mist of droplets of which less than about 10%, preferably less than about 5%, more preferably less than about 2%, have a diameter of less than about 10 µm, and wherein the droplets are characterized by (i) Dv(50) of between about 40 µm to about 150 µm, preferably between about 50 µm to about 120 µm; and/or (ii) Dv(90) of less than about 350 µm. Droplet size distribution is measured using Laser diffraction method with Spraytec®.

A kit described herein may further comprise instruction for use, for example in the form of an insert or label.

Compositions or unit dose described herein may be useful for the treatment of pain, and particularly acute pain. The acute pain is selected from but not limited to breakthrough cancer pain, dental pain or pain associated with the medical conditions which include day care surgeries, appendicectomy, cholecystectomy, nailing, plating, fixation of fractured bone, burns dressing, jejunostomy dressing and wound dressing.

Described herein are processes for preparing compositions. Composition can be in the form of a dry powder with suitable particle size or can be in liquid form. Preferably, a unit dose or a composition is in liquid form, which can be a suspension, a solution or a dispersion. The process comprises the step of mixing tapentadol or its pharmaceutically acceptable salt(s) with at least one nasal carrier. Tapentadol or its pharmaceutically acceptable salt(s) and nasal carrier can be mixed in any order to prepare final mixture, solution, suspension or dispersion. In an embodiment, a composition or a unit dose is prepared by mixing a mucoadhesive agent and a solubilizer to prepare a solution or a dispersion; adding tapentadol or its pharmaceutically acceptable salt with said solution or dispersion. Optionally drying the solution or the dispersion with a suitable drying technique including freeze drying or spray drying.

The compositions or unit dose described herein can be administered through a nasal spray or any suitable nasal applicator. Nasal composition can be of multi dose container or unit dose container, preferably in multi dose container.

EXAMPLES

Aspects of the disclosure are illustrated by the following examples.

Examples 1-4

Tapentadol Hydrochloride Formulations

| Ingredient | Example | | | |
| --- | --- | --- | --- | --- |
| | Ex. 1 %, w/v | Ex. 2 %, w/v | Ex. 3 %, w/v | Ex. 4 %, w/v |
| Tapentadol Hydrochloride | 17.5% | 22.5% | 25% | 38.5% |
| Hypromellose | 0.1% | 0.1% | 0.1% | 0.1% |
| Poloxamer 188 | 0.6% | 0.6% | 0.6% | 0.6% |
| Neotame | 0.5% | 0.5% | 0.5% | 0.5% |
| Benzalkonium chloride solution | 0.02% | 0.02% | 0.02% | 0.02% |

-continued

|  | Example | | | |
|---|---|---|---|---|
| Ingredient | Ex. 1 %, w/v | Ex. 2 %, w/v | Ex. 3 %, w/v | Ex. 4 %, w/v |
| Novamint spearmint flavour | 0.1% | 0.1% | 0.1% | 0.1% |
| Purified water | Q.s. to 100% | Q.s. to 100% | Q.s. to 100% | Q.s. to 100% |
| pH | 4.66 | 4.63 | 4.65 | 4.44 |
| Packaging[a] | 100 μL | 100 μL | 100 μL and 70 μL | 100 μL and 140 μL |
| Delivered dose | 17.5 mg/spray | 22.5 mg/spray | 25 mg/spray and 17.5 mg/spray | 38.5 mg/spray and 50 mg/spray |

[a]Filled in Multidose container with specified volume nasal pump.

The respective concentrations of tapentadol hydrochloride in the exemplified embodiments are: Ex. 1 (175 mg/mL), Ex. 2 (225 mg/mL), Ex. 3 (250 mg/mL), and Ex. 4 (385 mg/mL). In certain instances, it is convenient to determine the concentration of tapentadol in the respective exemplified embodiments. This may be achieved by multiplying the concentration of tapentadol hydrochloride by the molecular weight of tapentadol free base (221.34 mg/mmol), and then dividing by the molecular weight of tapentadol hydrochloride (257.80 mg/mmol). In view of this relationship, the respective concentrations of tapentadol (free base) in the exemplified embodiments are: Ex. 1 (150.3 mg/mL), Ex. 2 (193.2 mg/mL), Ex. 3 (214.6 mg/mL), and Ex. 4 (330.6 mg/mL).

Procedure: Tabulated quantity of hypromellose (hydroxypropyl methylcellulose) was dissolved in purified water. Poloxamer 188 was added into the obtained solution and stirred to form homogenous solution. In the obtained solution, neotame was added. Tapentadol hydrochloride was dissolved in obtained solution, followed by addition of benzalkonium chloride and novamint spearmint flavor. Volume of the solution was made up with purified water.

Spray Patterns

| Example | Ex. 1[a] | | Ex. 2[a] | | Ex. 3[a] | | Ex. 4[a] | | Ex. 4[b] | |
|---|---|---|---|---|---|---|---|---|---|---|
| Distance | D, cm | | D, cm | | D, cm | | D, cm | | D, cm | |
|  | 2.5 | 5 | 2.5 | 5 | 2.5 | 5 | 2.5 | 5 | 2.5 | 5 |
| Ovality ratio | 1.03 | 1.08 | 1.03 | 1.02 | 1.00 | 1.04 | 1.07 | 1.09 | 1.13 | 1.06 |
| Dmax, cm | 3.2 | 4.9 | 3.2 | 4.9 | 3.5 | 4.9 | 3.8 | 4.5 | 3.3 | 6.4 |
| Dmin, cm | 3.1 | 4.5 | 3.1 | 4.8 | 3.5 | 4.7 | 3.0 | 4.1 | 2.9 | 5.8 |

[a]Pump used: Aptar 100 μL CPS pump (at 2.5 cm and 5 cm distances).
[b]Pump used: Aptar 140 μL CPS pump (at 2.5 cm and 5 cm distances).

Droplet size distribution (DSD) by laser diffraction

| Ex. | D, cm | Dv(10), μm | Dv(50), μm | Dv(90), μm | Span | % V < 10μ (%) |
|---|---|---|---|---|---|---|
| Ex. 1 | 3 | 23.98 | 62.30 | 153.13 | 78.35 | 2.07 |
|  | 6 | 31.12 | 61.40 | 134.70 | 76.29 | 1.69 |
| Ex. 2 | 3 | 24.84 | 65.70 | 162.77 | 83.26 | 2.10 |
|  | 6 | 30.80 | 60.80 | 135.13 | 75.19 | 1.72 |
| Ex. 3[a] | 3 | 29.85 | 86.57 | 182.97 | 1.76 | 0.55 |
|  | 6 | 35.05 | 79.36 | 169.60 | 1.69 | 0.56 |
| Ex. 3[b] | 3 | 32.99 | 95.42 | 191.73 | 105.43 | 1.66 |
|  | 6 | 30.91 | 77.35 | 173.13 | 91.26 | 1.84 |
| Ex. 4[a] | 3 | 35.20 | 112.60 | 232.20 | 1.74 | 0.43 |
|  | 6 | 35.93 | 96.25 | 208.93 | 1.79 | 0.91 |
| Ex. 4[c] | 3 | 36.23 | 116.27 | 284.57 | 2.13 | 0.57 |
|  | 6 | 34.97 | 102.01 | 241.07 | 1.99 | 1.11 |

[a]100 μL Pump.
[b]70 μL Pump.
[c]140 μL Pump.

Effect of device parameters: The observed spray patterns for each composition shows that the ovality ratio is about 1, which signifies that at different distances of administration the spray pattern remains the same, and which assures the effective distribution of droplets in nostril(s) and thus reducing the variability in absorption. The observed droplet size distribution (DSD) values for each composition shows effective formation of droplet size. Generally, smaller droplets tend to deposit in the lower turbinate in nasal mucosa which is having slower clearance than middle and upper turbinate, for systemic delivery it is always preferable that maximum deposition to be carried out in middle turbinate.

Comparative Examples 1-4

Single Dose PK Parameters of Oral Formulation
(Source Nucynta® FDA Clinical Pharmacology and
Biopharmaceutics Review ("CPBR") for NDA
22-304)

| Parameters | Comp. Ex. 1 For 21.5 mg[a] | Comp. Ex. 2 DN to 19.3 mg[a] | Comp. Ex. 3 For 100 mg[c] | Comp. Ex. 4 DN to 50 mg[d] |
|---|---|---|---|---|
| Cmax (ng/ml) | 17.1 ± 6.7 | 15.3 ± 6.0 | 95.1 ± 21.3 | 47.6 ± 10.6 |
| $AUC_{0-6}$ (hr · ng/ml) | 57.5 ± 23.3 | 51.6 ± 20.9 | 299 ± 87.5 | 149.5 ± 43.7 |

[a]Sect. 2.3.2.2 of CPBR (Study KF5503/08).
[b]Dose Normalized (DN) values calculated from 21.5 mg values using a proportion and propagating errors.
[c]Sect. 2.2.5.3 of CPBR (Study HP5503/13).
[d]DN values calculated from 100 mg values using a proportion and propagating errors.

A 50-mg dose tapentadol free base is equivalent to 58.24-mg dose of tapentadol hydrochloride, while a 100-mg dose of tapentadol free base is equivalent to 116.48-mg tapentadol hydrochloride.

Pharmacokinetic Data after Nasal Administration

Formulations were tested in human for the following objectives: (i) dose reduction from intranasal route in comparison to oral administration; (ii) effect of administration volume; (iii) effect of concentration; and (iv) effect of surface area.

In a pharmacokinetic (PK) study, 4 groups having eight (6+2) healthy adults each, were given an intranasal dosage level as summarized below.

| Dose Level | Ex. Formulation | Dosage Volume | Tap HCl (mg) | Tap FB (mg) |
|---|---|---|---|---|
| 3S | 3 (250 mg/mL) | 70 µL in single nostril | 17.5 | 15 |
| 2S | 2 (225 mg/mL) | 100 µL in single nostril | 22.5 | 19.3 |
| 3B | 3 (250 mg/mL) | 70 µL in both nostrils | 35 | 30 |
| 2B | 2 (225 mg/mL) | 100 µL in both nostrils | 45 | 38.6 |

Samples were collected prior to administration and up to 16-hrs post-dosing. Samples were analyzed for tapentadol content using LC-MS/MS. The PK data from that study are shown in the following table.

Pharmacokinetic data of Formulation Examples 2 and 3

| Parameters | Dose Level 3S, 17.5 mg/70 µL | Dose Level 2S, 22.5 mg/100 µL | Dose Level 3B, (17.5 mg/70 µL) * 2 | Dose Level 2B, (22.5 mg/100 µL) * 2 |
|---|---|---|---|---|
| Tmax (hr) | 0.50 (0.25-0.50) | 0.63 (0.08-1.50) | 0.12 (0.08-1.0) | 0.25 (0.16-0.50) |
| Cmax (ng/ml) | 44.76 ± 22.52 | 50.78 ± 41.0 | 112.07 ± 53.53 | 123.16 ± 54.39 |
| $AUC_{0-6}$ (hr · ng/ml) | 120.57 ± 37.73 | 145.42 ± 60.70 | 266.25 ± 97.91 | 290.19 ± 60.33 |
| AUCt (hr · ng/ml) | 173.46 ± 52.19 | 213.84 ± 81.63 | 379.23 ± 129.26 | 415.54 ± 82.28 |
| AUCinf (hr · ng/ml) | 185.20 ± 55.42 | 228.35 ± 85.52 | 400.51 ± 130.43 | 446.93 ± 89.33 |

FIG. 1 displays the mean plasma concentration (ng/mL) after the administration of: (i) Ex. 3 formulation at Dose Level 3S, 17.5 mg tapentadol hydrochloride (equivalent to 15 mg tapentadol free base) administered to a single (S) nostril using a dosage volume of 70 µL; (ii) Ex. 2 formulation at Dose Level 2S, 22.5 mg tapentadol hydrochloride (equivalent to 19.3 mg tapentadol free base) administered to single (S) nostril using a dosage volume of 100 µL; and (iii) Comp. Ex. 4 (oral administration of immediate release composition containing 50 mg tapentadol free base).

Figure 2:
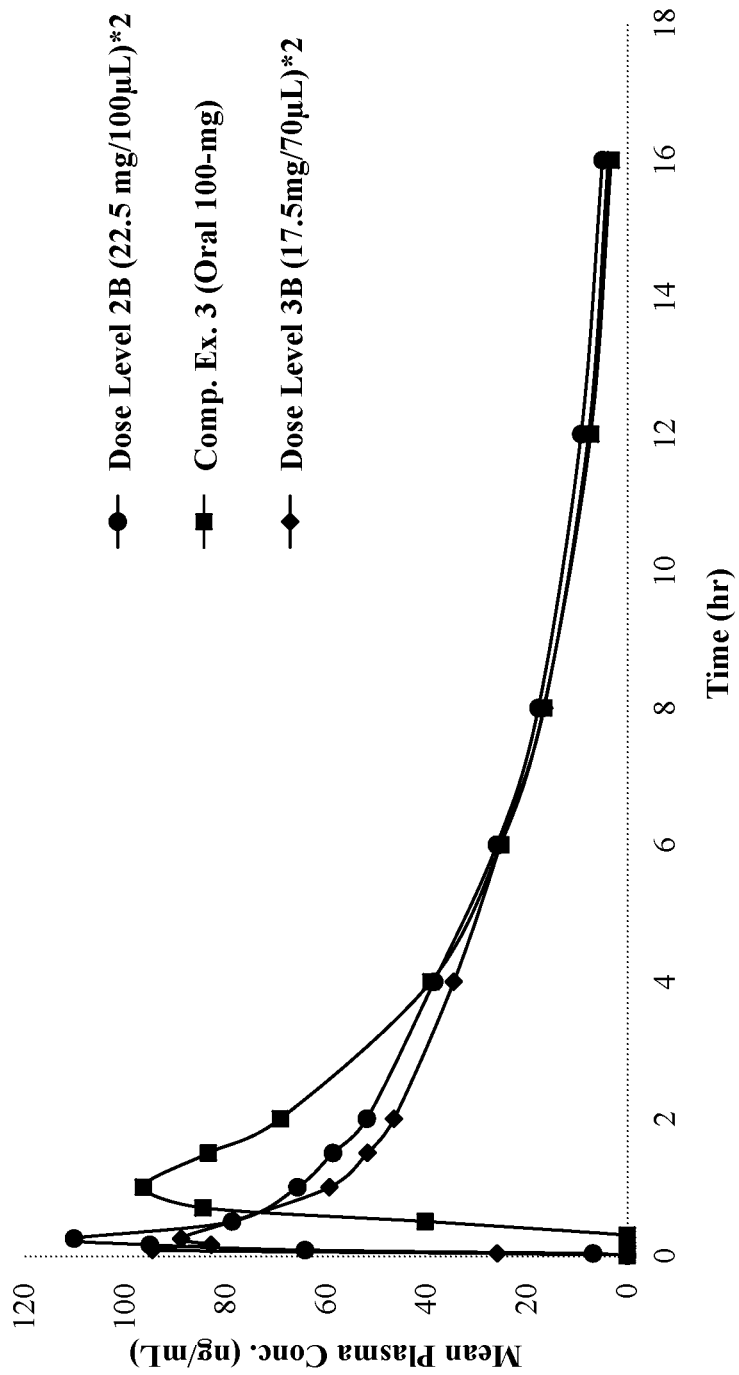
FIG. 2 displays the mean plasma concentration (ng/mL) for Ex. 3 formulation at Dose Level 3B (17.5 mg/70 µL)*2 (administered to each nostril), Ex. 2 formulation at Dose Level 2B (22.5 mg/100 µL)*2 (administered to each nostril)), and Comp. Ex. 3 Oral 100 mg (free base equivalent).

FIG. 2 displays the mean plasma concentration (ng/mL) after the administration of: (i) Ex. 3 formulation at Dose Level 3B, 17.5 mg tapentadol hydrochloride administered to both (B) nostrils using a dosage volume of 70 µL for each nostril (total dosage amount: 35 mg tapentadol hydrochloride (equivalent to 30 mg tapentadol free base); (ii) Ex. 2 formulation at Dose Level 2B, 22.5 mg tapentadol hydrochloride administered to both (B) nostrils using a dosage volume of 100 µL for each nostril (total dosage amount: 45 mg tapentadol hydrochloride (equivalent to 38.6 tapentadol free base); and (iii) Comparative Example 3 (oral administration of immediate release composition containing 100 mg tapentadol free base).

Based on the results presented for Dose Level 2S compared to Comparative Example, 1, it can be seen that a single dose at Dose Level S (i.e., 19.3 mg tapentadol free base) achieves a maximum plasma concentration of 50.78±41.0 ng/mL, while the same amount of orally administered tapentadol achieves a Cmax of about 15.3 ng/mL. Accordingly, the mean Cmax value achieved by intranasally administering Dose Level 2S is at least about two-times greater than the mean Cmax achieved by orally administering to a human a single dose of an immediate release composition comprising tapentadol or a pharmaceutically acceptable salt thereof in an amount that is equivalent to about 19.3 mg tapentadol free base. More specifically, the mean Cmax value achieved by intranasally administering Dose Level 2S is about three-times greater than the mean Cmax achieved by orally administering to a human a single dose of an immediate release composition comprising tapentadol or a pharmaceutically acceptable salt thereof in an amount that is equivalent to about 19.3 mg tapentadol free base.

Based on the results presented for Dose Levels 2S and 2B compared to Comparative Examples 4 and 3, respectively, the following conclusions may be readily ascertained. Early onset of action was achieved with intranasal formulation versus oral formulation. The observed PK parameters for Dose Level 2S (Ex. 2 Formulation at total dosage amount of 22.5 mg tapentadol hydrochloride (equivalent to 19.3 mg tapentadol free base)) were comparable to the PK parameters normalized for Comparative Ex. 4 (oral formulation 50 mg tapentadol free base). The observed PK parameters for Dose Level 2B (Ex. 2 Formulation at total dosage amount of 45 mg tapentadol hydrochloride (equivalent to 38.6 mg tapentadol free base)) were comparable to the PK parameters observed for Comparative Ex. 3 (oral formulation 100 mg tapentadol free base).

Alternative embodiments, examples, and modifications which would still be encompassed by the disclosure may be made by those skilled in the art, particularly in light of the foregoing teachings. Further, it should be understood that the terminology used to describe the disclosure is intended to be in the nature of words of description rather than of limitation.

The subject matter of U.S. patent application Ser. No. 14/233,265 and of U.S. Provisional Patent Application No. 62/444,900 is incorporated by reference in its entirety. Additionally, the references described herein are incorporated by reference in their entirety to the extent necessary. In the event that there is a difference in meaning between the incorporated terms and the terms disclosed herein, the meaning of the terms disclosed herein will control.

Those skilled in the art will also appreciate that various adaptations and modifications of the preferred and alternative embodiments described above can be configured without departing from the scope and spirit of the disclosure. Therefore, it is to be understood that, within the scope of the embodiments described herein, the disclosure may be practiced other than as specifically described herein.

We claim:

1. A unit dose comprising:
    tapentadol or a pharmaceutically acceptable salt thereof in an amount that is equivalent to about 19.3 mg tapentadol free base and at least one nasal carrier;
    wherein after intranasal administration to one nostril of a human, a tapentadol mean Cmax-value achieved by said unit dose ranges from about 40 ng/mL to 65 ng/mL.

2. The unit dose of claim 1, wherein after intranasal administration to the human, a tapentadol mean AUC0-6-value achieved by said unit dose ranges from about 115 hr*ng/mL to 182 hr*ng/mL.

3. The unit dose of claim 1, wherein the tapentadol mean Cmax-value achieved by intranasally administering said unit dose is equivalent to or greater than the tapentadol mean Cmax-value achieved by orally administering to a human a single dose of an immediate release composition comprising tapentadol or a pharmaceutically acceptable salt thereof in an amount that is equivalent to about 50 mg tapentadol free base.

4. The unit dose of claim 1, wherein the tapentadol mean Cmax-value achieved by intranasally administering said unit dose is at least about two-times greater than the tapentadol mean Cmax-value achieved by orally administering to a human a single dose of an immediate release composition comprising tapentadol or a pharmaceutically acceptable salt thereof in an amount that is equivalent to about 19.3 mg tapentadol free base.

5. A unit dose comprising:
    tapentadol or a pharmaceutically acceptable salt thereof in an amount that is equivalent to about 19.3 mg tapentadol free base and at least one nasal carrier;
    wherein after intranasal administration to two nostrils of a human a tapentadol mean Cmax-value achieved by said unit dose ranges from about 98 ng/mL to 155 ng/mL.

6. The unit dose of claim 5, wherein after intranasal administration to each nostril of the human, a tapentadol mean AUC0-6-value achieved by said unit dose ranges from about 230 hr*ng/mL to 365 hr*ng/mL.

7. The unit dose of claim 5, wherein the tapentadol mean Cmax-value achieved by intranasally administering said unit dose to each nostril is equivalent to or greater than the tapentadol mean Cmax-value achieved by orally administering to a human a single dose of an immediate release composition comprising tapentadol or a pharmaceutically acceptable salt thereof in an amount that is equivalent to about 100 mg tapentadol free base.

8. The unit dose of claim 1, wherein the nasal carrier is selected from about 0.05 to about 5% w/v of a mucoadhesive agent; from about 0.2 to 10.0% w/v of a solubilizer; from about 0.1% to 1% of a sweetener; from about 0.01 to 1% w/v of a preservative, from about 0.01% w/v to 0.5% w/v of a flavouring agent and a sufficient amount of a water vehicle.

9. The unit dose of claim 8, wherein the mucoadhesive agent is selected from hydroxypropylmethyl cellulose and carboxymethyl cellulose or its pharmaceutically acceptable salt, the solubilizer comprises a poloxamer, the sweetener is selected from sucralose and neotame, preservative comprises benzalkonium chloride and the flavouring agent comprises a spearmint flavour.

10. A method of treating pain in a human in need thereof, which comprises:
    intranasally administering to the human a unit dose comprising tapentadol or a pharmaceutically acceptable salt thereof;
    wherein the amount of tapentadol or a pharmaceutically acceptable salt thereof in said unit dose is equivalent to about 19.3 mg tapentadol free base; and
    wherein after intranasal administration of the unit dose, a tapentadol mean Cmax-value achieved by said intranasal administration ranges from about 40 ng/mL to 65 ng/mL.

11. The method of claim 10, wherein a tapentadol mean AUC0-6-value achieved by said intranasal administration ranges from about 115 hr*ng/mL to 182 hr*ng/mL.

12. The method of claim 10, wherein intranasal administration is in a single nostril.

13. The method of claim 10, wherein the tapentadol mean Tmax-value achieved by said intranasal administration is about 1 hr or less.

14. The method of claim 10, wherein the tapentadol mean Cmax-value achieved by said intranasal administration is equivalent to or greater than the tapentadol mean Cmax-value achieved by orally administering to a human a single dose of an immediate release composition comprising tapentadol or a pharmaceutically acceptable salt thereof in an amount that is equivalent to about 50 mg tapentadol free base.

15. The method of claim 10, wherein the tapentadol mean Cmax-value achieved by intranasally administering said unit dose is at least about two-times greater than the tapentadol mean Cmax-value achieved by orally administering to a human a single dose of an immediate release composition comprising tapentadol or a pharmaceutically acceptable salt thereof in an amount that is equivalent to about 19.3 mg tapentadol free base.

16. A method of treating pain in a human in need thereof, which comprises:
    intranasally administering to the human a unit dose comprising tapentadol or a pharmaceutically acceptable salt thereof;
    wherein the amount of tapentadol or a pharmaceutically acceptable salt thereof in said unit dose is equivalent to about 19.3 mg tapentadol free base; and
    wherein after intranasal administration of the unit dose, a tapentadol mean Cmax-value achieved by said intranasal administration to each nostril, ranges from about 98 ng/mL to 155 ng/mL.

17. The method of claim 16, wherein a tapentadol mean AUC0-6-value achieved by said intranasal administration to each nostril, ranges from about 230 hr*ng/mL to 365 hr*ng/mL.

18. The method of claim 16, wherein the tapentadol mean Tmax-value achieved by said intranasal administration is about 1 hr or less.

19. The method of claim 16, wherein the tapentadol mean Cmax-value achieved by said intranasal administration to each nostril is equivalent to or greater than the tapentadol mean Cmax-value achieved by orally administering to a human a single dose of an immediate release composition comprising tapentadol or a pharmaceutically acceptable salt thereof in an amount that is equivalent to about 100 mg tapentadol free base.

20. The method of claim 16, wherein intranasal administration is in two nostrils.

* * * * *